United States Patent [19]

Krapf et al.

[11] 4,237,320

[45] Dec. 2, 1980

[54] 1,3-BIS-ARYL-2-OXYALKYLATED-GLYCEROL ETHERS

[75] Inventors: Heinz Krapf, Grünstadt; Knut Oppenlaender, Ludwigshafen; Guenter Uhl, Worms, all of Fed. Rep. of Germany

[73] Assignee: BASF Aktiengesellschaft, Fed. Rep. of Germany

[21] Appl. No.: 69,920

[22] Filed: Aug. 27, 1979

[30] Foreign Application Priority Data

Sep. 11, 1978 [DE] Fed. Rep. of Germany ....... 2839463

[51] Int. Cl.³ .................... C07C 43/164; C09D 11/02
[52] U.S. Cl. ...................................... 568/609; 106/22
[58] Field of Search ......................................... 568/609

[56] References Cited

U.S. PATENT DOCUMENTS

| | | | |
|---|---|---|---|
| 1,979,144 | 10/1934 | Dahlen et al. | 568/609 |
| 2,903,485 | 9/1959 | Lane et al. | 568/609 |
| 3,408,404 | 10/1968 | Vandenburg | 568/609 |
| 3,494,939 | 2/1970 | Smith | 568/609 |
| 3,928,688 | 12/1975 | Dachs et al. | 428/515 |

FOREIGN PATENT DOCUMENTS 2139447 2/1972 Fed. Rep. of Germany .
2139448 2/1972 Fed. Rep. of Germany .

OTHER PUBLICATIONS

Piantadosi et al., "J. Med. Chem.", vol. 19 (1976), pp. 222-229.

*Primary Examiner*—Joseph E. Evans
*Attorney, Agent, or Firm*—Keil & Witherspoon

[57] ABSTRACT

Oxyalkylated 1,3-bis-aryl-glycerol ethers of the formula

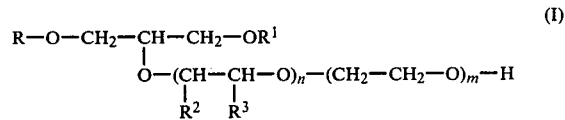

where R and $R^1$ are aromatic substituents, $R^2$ is $-CH_3$ or $-C_2H_5$, $R^3$ is $-H$ or $-CH_3$, n is from 0 to 10 and m is from 8 to 50.

The compounds of the formula I are used as emulsifiers, preferably in the preparation of print pastes.

1 Claim, No Drawings

1,3-BIS-ARYL-2-OXYALKYLATED-GLYCEROL ETHERS

The present invention relates to oxyalkylated 1,3-bis-aryl-glycerol ethers and to their use as emulsifiers.

German Laid-Open Applications DOS 2,139,447 and DOS 2,139,448 disclose oxyalkylated 1,3-glycerol ethers wherein one or more ether radical is derived from an alkyl group. These substances are surfactants. 1,3-bis-Aryl-glycerol ethers are also known, cf. J. Med. Chem. 19 (1976), 222-229. This publication describes the oxidation of the 1,3-bis-aryl-glycerol ethers to give 1,3-bis-aryl-2-propanones.

German Patent 2,128,904 relates to a process for printing fiber materials with print pastes based on oil-in-water emulsions, organic pigments, thickeners, pigment binders and emulsifiers of the oxyalkylated phenol derivative type. The emulsifiers used are di-(α-phenylethyl)-phenols oxyethylated with from 12 to 16 molecules of ethylene oxide. It is true that these compounds are very good emulsifiers, but they do not ensure reproducible print quality in every case.

It is an object of the invention to provide highly efficient emulsifiers which, when used in print pastes based on oil-in-water emulsions, ensure good reproducibility of print quality.

We have found that this object is achieved, according to the invention, with oxyalkylated 1,3-bis-aryl-glycerol ethers of the formula

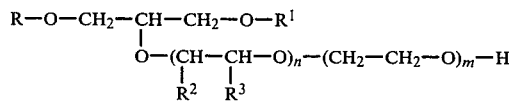

where R and R$^1$ are

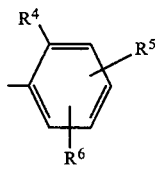

α-naphthyl or β-naphthyl and R$^4$, R$^5$ and R$^6$ are —H,- C$_1$— to C$_{12}$-alkyl or

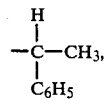

R$^2$ is —CH$_3$ or —C$_2$H$_5$, R$^3$ is —H or —CH$_3$, n is from 0 to 10 and m is from 8 to 50. The novel compounds are water-soluble and are used as oil-in-water emulsifiers, preferably for the preparation of print pastes.

The compounds according to the invention are prepared by reacting 2 moles of phenol or of a phenol derivative with 1 mole of alkali, then reacting the phenol/phenolate mixture with 1 mole of epichlorohydrin, and, after separating off the alkali metal salt which has precipitated, subjecting the reaction mixture to an oxyalkylation.

Examples of phenols suitable for reaction with epichlorohydrin are phenol itself, C$_1$–C$_{12}$-alkyl-substituted phenols, eg. cresols, xylenols, p-tert.-butylphenol, 2,4-di-tert.-butylphenol, octylphenol and nonylphenol, α-phenylethyl-phenol, bis-(α-phenylethyl)-phenol, tris-(α-phenylethyl)-phenol, α-naphthol and β-naphthol. If only one phenol is used in the reaction of the epichlorohydrin with the phenol/phenolate mixture, the substituent R in formula I is identical with the substituent R$^1$. However, in preparing the glycerol ethers, isomer mixtures of phenols, or different phenols, may also be used. In these cases the substituents R and R$^1$ have different meanings. The preferred phenols used for the preparation of the glycerol ethers are xylenols, for example 2,4-xylenol, 2,5-xylenol, 2,3-xylenol, 3,4-xylenol and 3,5-xylenol.

The glycerol ethers can be prepared in the absence of a solvent by heating the phenol/phenolate mixture and the epichlorohydrin. In that case, the reaction takes place in the melt. However, it is also possible to use inert diluents, such as dioxane, benzene or toluene, or alcohols, eg. isopropanol, isobutanol and isoamyl alcohol, or to carry out the reaction in water as the solvent. Where R and R$^1$ in formula I are different substituents, 1 mole of a phenolate is first reacted with 1 mole of epichlorohydrin, and the aryl glycidyl ether thus produced is isolated and is then reacted with one mole of a phenol different from the first phenol, using boron trifluoride as the catalyst, to give the 1,3-bis-aryl-glycerol ether.

The 1,3-bis-aryl-glycerol ethers thus prepared still contain a free OH group which can be oxyalkylated. The oxyalkylation reaction is carried out in the conventional manner by reacting the 1,3-bis-aryl-glycerol ether, containing an OH group, with an alkylene oxide. The preferred alkylene oxide is ethylene oxide. Per mole of 1,3-bis-aryl-glycerol ether, from 8 to 50 moles, preferably from 14 to 30 moles, of ethylene oxide are used. Effective emulsifiers are also obtained if the 1,3-bis-aryl-glycerol ethers, prepared from 2 moles of a phenol and 1 mole of epichlorohydrin, are first allowed to react with propylene oxide or butylene oxide, and the reaction product is subsequently reacted with from 8 to 50 moles of ethylene oxide. Propylene oxide and the isomeric butylene oxides are employed in an amount of up to 10 moles per mole of the 1,3-bis-aryl-glycerol ether containing hydroxyl groups. In that case, n in formula I is 10. If propylene oxide and butylene oxides, or mixtures of these, are used in the oxyalkylation, the content of ethylene oxide units in the oxyalkylated 1,3-bis-aryl-glycerol ethers is preferably from 20 to 50 (m in formula I is then from 20 to 50). The oxyalkylation can also be carried out with a gas mixture, for example of propylene oxide and ethylene oxide. As a rule, the oxyalkylation of the glycerol ether is carried out in the presence of an alkaline catalyst at above 100° C., for example at from 110° to 130° C. However, it can also be carried out in the presence of acid catalysts, for example Lewis acids, eg. BF$_3$-etherates.

Whilst oxyalkylated 1,3-bis-alkyl-glycerol ethers are definitely to be regarded as surfactants, the oxyalkylated 1,3-bis-aryl-glycerol ethers according to the invention are efficient emulsifiers. For example, the novel compounds can be used for emulsifying gasoline, white oil, dibutyl phthalate, castor oil, heptane, toluene, perchloroethylene or etherified methylolmelamine. In addition, the novel compounds have the property of keeping solid water-insoluble particles, such as pigments and dyes, in a finely dispersed state. They prevent agglomeration and/or flocculation of the particles.

A particularly important use of the novel compounds is as emulsifiers for the preparation of print pastes, more especially pigment print pastes containing little or no gasoline. The novel compounds may also be used as emulsifiers for the preparation of print pastes based on oil-in-water emulsions. The oil phase of the print paste is in the main formed by gasoline fractions boiling at from 80° to 250° C. However, pure hydrocarbons, eg. the hexanes, heptanes, nonanes, cyclohexylbenzenes, benzene, toluene or xylenes may also be used as the oil phase of the print pastes. Mixtures of hydrocarbons are also suitable for this purpose. In addition to water and the organic solvent, the print pastes contain a thickener as a further constituent. The thickeners are in the main water-soluble or water-swellable thickeners, such as alginates, locust bean ether, starch ether or carboxymethylcellulose. Examples of particularly effective compounds are the synthetic thickeners disclosed in German Laid-Open Application DOS 2,054,885. These thickeners are derived from diurethanes and polyurethanes of polyether-diols. They are described in detail in the said DOS and can also be used together with the emulsifiers according to the invention for the preparation of the print pastes. Depending on the desired viscosity of the print pastes, the latter contain from about 0.02 to 1% by weight, preferably from 0.05 to 0.5% by weight, based on the final paste, of the said synthetic thickeners. Thickeners of natural origin are employed in larger amounts, for example of up to 8%.

In addition, the print pastes in general contain the binders conventionally used for textile printing, for example those disclosed in German Patent 1,140,898. The binders are preferably synthesized from monomers which give polymers which are soft and elastic at room temperature, for example vinyl esters of higher carboxylic acids, eg. vinyl propionate, acrylic acid esters and methacrylic acid esters, and butadiene or its homologs. These monomers are either homopolymerized or copolymerized with one another, or copolymerized with yet other monomers, for example with maleic acid esters, fumaric acid esters, vinyl ethers, vinylketone, styrene, vinyl chloride, vinylidene chloride, vinyl acetate, acrylonitrile or methyl methacrylate. In addition, small amounts of watersoluble polymerizable compounds, such as acrylic acid, vinylpyrrolidone, amides of unsaturated acids or the N-methylol compounds or N-methylol ethers of these amides may be present as copolymerized units. The binders may contain yet other comonomers which possess one or more polymerizable double bonds, for example esters of $\alpha,\beta$-ethylenically unsaturated organic acids, eg. acrylic acid or methacrylic acid, with higher alcohols which have a halogen in the $\beta$-position to a free hydroxyl group, eg. 3-chloropropane-1,2-diol, 2,3-dichlorobutane-1,4-diol or 3-chloro-2-chloromethyl-propane-1,2-diol.

The assistants conventionally used for the preparation of print pastes, for example defoamers, pH regulators, plasticizers and water-soluble precondensates, may be used in the preparation of the oil-in-water emulsions. Defoamers are usually employed in amounts of from 0.01 to 0.15% by weight, based on the finished print paste. Examples of suitable defoamers are block copolymers of ethylene oxide and 1,2-propylene oxide which are etherified with a polyhydric alcohol and additionally esterified with a carboxylic acid. Such products are disclosed, for example, in German Published Application DAS 2,114,609.

The finished print paste is obtained in the conventional manner by, for example, stirring a thickened emulsion, which in addition to water contains a solvent and the emulsifier according to the invention and may or may not contain a defoamer, with an organic pigment or pigment formulation and a suitable binder, with or without an additional, water-soluble thickener and other print paste constituents conventionally used in practice. However, it is also possible for some of the print paste constituents to be present in the aqueous emulsifier solution before the solvent is emulsified therein. If a print paste has turned out too thin, thickener may also be added subsequently. A print paste can be prepared by first preparing a thickener emulsion by mixing the emulsifier, an emulsion thickener, water and heavy gasoline, in which a defoamer may or may not be dissolved, by vigorous stirring.

A ready-to-use pigment print paste for roller printing is obtained, for example, by stirring together 60 parts of an organic pigment formulation (containing 30% of a colored pigment), 790 parts of the thickener emulsion described above and 120 parts of a pigment binder, based on one of the above copolymers, in the form of an aqueous dispersion, with or without from 10 to 40 parts of a 33% strength aqueous solution of diammonium hydrogen phosphate as an acid donor. 1,000 parts by weight of print paste as a rule contain from 0.1 to 40 parts by weight of organic pigment, from 30 to 100 parts by weight of a 100% strength binder and from 150 to 650 parts by weight of a hydrocarbon oil as the essential constituents.

The novel emulsifiers permit the preparation of very stable print pastes. Prints produced with such pastes are very level and bright. The prints exhibit excellent definition both in screen printing and in roller printing. The print pastes are, in particular, also suitable for rotary screen printing. It is an advantage that the print pastes not only contain merely small amounts of emulsion thickeners as described, for example, in German Laid-Open Application DOS 2,054,885, but are also low-foaming during their preparation, have a good shelf life, and are stable to shearing forces. The print pastes prepared with the novel emulsifiers can in the main be used for pigment printing on cotton, rayon, wool, glass fiber fabrics and other natural and synthetic fibers, as well as on a wide variety of union fabrics. However, it is also possible to prepare the print pastes with, for example, conventional dyes, eg. disperse dyes or reactive dyes.

The Examples which follow illustrate the invention. Parts and percentages in the Examples are by weight.

EXAMPLE 1

Preparation of the oxyalkylated 1,3-bis-aryl-glycerol ethers 610 parts (5 moles) of 2,5-dimethylphenol and 300 cm$^3$ of dioxane are heated to 50°–60° C. whilst stirring, and at this temperature 110 parts (2.75 moles) of sodium hydroxide powder are added. The temperature is then raised to 90°–95° C. The mixture is stirred at this temperature for 2 hours. 231 parts (2.5 moles) of epichlorohydrin are then run in over 30 minutes, after which the mixture is refluxed for 4 hours. The sodium chloride which has precipitated is filtered off and the dioxane is distilled off under reduced pressure. 688 parts by weight of 1,3-bis-(2,5-dimethylphenyl)-glycerol ether are obtained.

986 parts (3.29 moles) of 1,3-bis-(2,5-dimethylphenyl)-glycerol ether are mixed with 8 parts of potassium hydroxide and reacted, in a stirred autoclave, at from 110° to 120° C., with 2600 parts (59 moles) of ethylene oxide added in portions. The pressure is from 4 to 9 bar. 3590 parts of a pale yellow pasty substance having excellent emulsifier properties are obtained.

Using the procedure described above, the phenols R-OH and $R^1$-OH shown in the Table were reacted with epichlorohydrin, the molar ratio being 1:1:1. The degree of oxyethylation m is also shown in the Table. This index indicates that 1 mole of the hydroxyl-containing 1,3-bis-aryl-glycerol ether has been reacted with m moles of ethylene oxide. In contrast to the emulsifiers known from German Patent 2,128,904, isomer mixtures, eg. isomeric xylenols, can be employed in the preparation of the compounds according to the invention without reducing the emulsifying efficiency of the oxyalkylated products. Whilst in the conventional emulsifiers the alkylene oxide content lay within a very narrow range, it can, in the novel compounds, vary within a substantially broader range, for example a range of, preferably, from 14 to 30 ethylene oxide units.

TABLE

| Example | R—OH | $R^1$—OH | m |
| --- | --- | --- | --- |
| (a) | phenol | $R^1 = R$ | 10 |
| (b) | o-cresol | $R^1 = R$ | 16 |
| (c) | m-cresol | $R^1 = R$ | 18 |
| (d) | p-cresol | $R^1 = R$ | 22 |
| (e) | 4-ethylphenol | $R^1 = R$ | 20 |
| (f) | 2-isopropylphenol | $R^1 = R$ | 25 |
| (g) | 2,3-xylenol | $R^1 = R$ | 16 |
| (h) | 2,4-xylenol | $R^1 = R$ | 18 |
| (i) | 2,5-xylenol | $R^1 = R$ | 22 |
| (j) | 2,6-xylenol | $R^1 = R$ | 20 |
| (k) | 3,4-xylenol | $R^1 = R$ | 20 |
| (l) | 3,5-xylenol | $R^1 = R$ | 18 |
| (m) | 2,3,6-trimethylphenol | $R^1 = R$ | 24 |
| (n) | p-tert.-butylphenol | $R^1 = R$ | 16 |
| (o) | 2,4-di-tert.-butylphenol | $R^1 = R$ | 22 |
| (p) | octylphenol | $R^1 = R$ | 18 |
| (q) | nonylphenol | $R^1 = R$ | 26 |
| (r) | nonylphenol | p-tert.-butylphenol | 18 |
| (s) | nonylphenol | phenol | 26 |
| (t) | 2,4-di-tert.-butylphenol | phenol | 20 |
| (u) | α-phenylethylphenol | $R^1 = R$ | 20 |
| (v) | bis-(α-phenylethyl)-phenol | $R^1 = R$ | 30 |
| (w) | tris-(α-phenylethyl)-phenol | $R^1 = R$ | 50 |
| (x) | α-naphthol | $R^1 = R$ | 45 |
| (y) | β-naphthol | $R^1 = R$ | 50 |

Preparation of the print pastes

EXAMPLE 2

140 parts of water are mixed with 50 parts of a 5% strength aqueous solution of sodium alginate and 10 parts of the oxyethylated 1,3-bis-(2,5-dimethylphenyl)-glycerol ether described in Example 1. This mixture is stirred at about 3,000 rpm whilst slowly adding to it 650 parts of gasoline followed by 150 parts of a 40% strength aqueous dispersion of a copolymer of 60% of n-butyl acrylate, 25% of styrene, 10% of acrylonitrile, 4% of N-methylol acrylamide and 1% of acrylic acid. A viscous, very stable oil-in-water emulsion, which serves as the base for pigmentary printing inks, is obtained.

960 parts of the oil-in-water emulsion is mixed with 40 parts of a commercial aqueous pigment formulation (phthalocyanine paste) of about 40% strength. A very stable print paste is obtained, which conforms to the most stringent requirements. A rayon fabric is roller-printed with the print paste thus prepared. The print obtained exhibits particularly high color yield and good brightness.

EXAMPLE 3

40.0 parts of an about 30% strength aqueous colorant paste (C.I. 71,103), 115.0 parts of a commercial 6% strength aqueous solution of ammonium polyacrylate, 120.0 parts of a 40% strength aqueous dispersion of a copolymer of 80% of n-butyl acrylate, 15% of acrylonitrile, 4.5% of N-methylol acrylamide and 0.5% of acrylic acid, 10.0 parts of the oxyethylated 1,3-bis-arylglycerol ether, described in Example 1, as the emulsifier, 20.0 parts of a 50% strength urea solution, 0.5 part of triethanolamine, 3.0 parts of glycerol, 30.0 parts of i-decyl stearate and 661.5 parts of water are mixed, and homogenized by stirring. A stable, very easily processable gasoline-free print paste, which does not contain any troublesome agglomerates, is obtained.

A cotton fabric is printed with this print paste in the conventional manner on a conventional rotary screen printing machine. Deep bright prints result.

EXAMPLE 4

A partial emulsion is first prepared from the following constituents:

| | | |
| --- | --- | --- |
| Water | 165 | g |
| Emulsifier from Example 2 | 5 | g |
| 5% strength alginate thickener | 400 | g |
| Gasoline | 430 | g |
| | 1000 | g |

270 parts of water, 100 parts of urea, 10 parts of sodium 3-nitrobenzenesulfonate and 20 parts of sodium carbonate are added to 600 parts of this emulsion. This gives a stock thickener from which the ready-to-use print pastes are obtained by adding colorant. 970 parts of the stock thickener were mixed, in one case, with 30 g of the reactive dye C.I. No. 13,245 and in the other case with 30 g of the yellow reactive dye C.I. No. 61,205.

In both cases, stable print pastes were obtained and were screen-printed onto cotton. In each case, deep, luminous bright prints were obtained.

EXAMPLE 5

An emulsion was first prepared by mixing 400 parts of an 8% strength aqueous locust bean ether thickener, 330 parts of water, 10 parts of the emulsifier according to Example 1 and 10 parts of sodium 3-nitrobenzenesulfonate. 250 parts of gasoline were then emulsified in this mixture and the pH was brought to 5.5 by adding citric acid. 960 parts of the resulting emulsion were then mixed with 40 parts of the disperse dye C.I. No. 62,030.

Another print paste was prepared by mixing 960 parts of the above emulsion with 40 parts of the disperse dye C.I. No. 60,756. The print pastes were screen-printed onto a polyester satin fabric. The printed material was fixed for 6 minutes with live steam at 175° C. and then washed in the conventional manner. In both cases, the print obtained on the polyester satin fabric exhibited a deep color, a good color yield and freedom from specks.

We claim:

1. An oxyalkylated 1,3-bis-aryl-glycerol ether of the formula

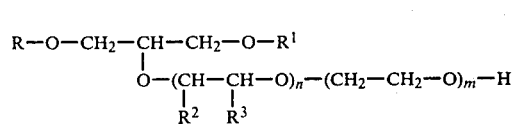
where R and R¹ are
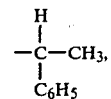
α-naphthyl or β-naphthyl and $R^4$, $R^5$ and $R^6$ are —H, $C_1$-$C_{12}$-alkyl or
$$-\underset{C_6H_5}{\overset{H}{\underset{|}{\overset{|}{C}}}}-CH_3,$$
$R^2$ is —$CH_3$ or —$C_2H_5$, $R^3$ is —H or —$CH_3$, n is from 0 to 10 and m is from 8 to 50.
* * * * *